(12) United States Patent
Hancke et al.

(10) Patent No.: US 11,986,458 B1
(45) Date of Patent: May 21, 2024

(54) NATURAL AND SYNTHETIC ANDROGRAPHOLIDES COMPOUNDS FOR THE TREATMENT OF SKELETAL MUSCULAR DYSTROPHIES

(71) Applicant: Innobiosciences LLC, Bradenton, FL (US)

(72) Inventors: Juan O. Hancke, Valdivia (CL); Enrique Brandan, Santiago (CL); Daniel Cabrera, Santiago (CL)

(73) Assignee: HP Ingredients Corp., Bradenton, FL (US)

( * ) Notice: Subject to any disclaimer, the term of this patent is extended or adjusted under 35 U.S.C. 154(b) by 1044 days.

(21) Appl. No.: 15/976,898

(22) Filed: May 11, 2018

(51) Int. Cl.
*A61K 31/365* (2006.01)
*A61K 9/00* (2006.01)
*A61P 21/00* (2006.01)

(52) U.S. Cl.
CPC .......... *A61K 31/365* (2013.01); *A61K 9/0053* (2013.01); *A61P 21/00* (2018.01)

(58) Field of Classification Search
CPC ...... A61K 31/365; A61K 9/0053; A61P 21/00
See application file for complete search history.

(56) References Cited

U.S. PATENT DOCUMENTS

| 2010/0144866 A1* | 6/2010 | Asami | A61K 36/18 514/473 |
|---|---|---|---|
| 2014/0271573 A1* | 9/2014 | Brandan | A61K 36/19 424/93.7 |

OTHER PUBLICATIONS

Kapsa, Robert. "Novel therapies for Duchenne muscular dystrophy." Lancet Neurol. 2003, 2:299-310.
Blau, Helen M. "Defective myoblasts identified in Duchenne muscular dystrophy." Proc Natl Acad Sci USA. 1983, 80:4856-4860.
Allen, David G. "Duchenne muscular dystrophy—what causes the increased membrane permeability in skeletal muscle?" Int J Biochem Cell Biol. 2011, 43:290-294.
Zhou, Lan. "Targeting fibrosis in Duchenne muscular dystrophy." J Neuropathol Exp Neurol. 2010, 69:771-776.
Desguerre, Isabelle. "Endomysial fibrosis in Duchenne muscular dystrophy . . . " J Neuropathol Exp Neurol. 2009, 68:762-773.
Wynn, Ta. "Cellular and molecular mechanisms of fibrosis." J Pathol. 2008, 214:199-210.
Varga, John. "Fibrosis Research: Methods and Protocols." Humana Press; 2005.
Verma, Sumit. "Review of Duchenne muscular dystrophy (DMD) for the pediatricians in the community." Clin Pediatr (Phila). 2010, 49:1011-1017.
Shen, Yuh-Chiang. "Andrographolide prevents oxygen radical production by human neutrophils . . . " Br J Pharmacol. 2002, 135:399-406.
Akbar, Shahid. "Andrographis paniculata: a review of pharmacological activities and clinical effects." Altern Med Rev. 2011, 16:66-77.
Rajagopal, Sriram. "Andrographolide, a potential cancer therapeutic agent isolated from Andrographis paniculata." J Exp Ther Oncol. 2003, 3:147-158.
Calabrese, Carlo. "A phase I trial of andrographolide in HIV positive patients and normal volunteers." Phytother Res. 2000, 14:333-338.
Xia, Yi-Feng. "Andrographolide attenuates inflammation by inhibition of NF-kappa B . . . " J Immunol. 2004, 173:4207-4217.
Acharyya, Swarnali. "Interplay of IKK/NF-kappaB signaling in macrophages and myofibers . . . " J Clin Invest. 2007, 117:889-901.
Cabrera, D. "Andrographolide attenuates skeletal muscle dystrophy in mdx mice and increases . . . " Skelet Muscle. 2014, 4:6.
Serrano, Antonio L. "Fibrosis development in early-onset muscular dystrophies: Mechanisms . . . " Semin Cell Dev Biol. 2017, 64:181-190.
Mendell, Jerry R. Molecular therapeutic strategies targeting Duchenne muscular dystrophy. J Child Neurol. 2010, 25:1145-1148.
Arechavala-Gomeza, Virginia. "Revertant fibres and dystrophin traces in Duchenne muscular dystrophy . . . " Neuromuscul Disord. 2010, 20:295-301.
Morales, Maria G. "CTGF/CON-2 over-expression can directly induce features of skeletal muscle dystrophy." J Pathol. 2011, 225:490-501.
Morales, Maria G. "Reducing CTGF/CCN2 slows down mdx muscle dystrophy . . . " Hum Mol Genet. 2013, 22:4938-4951.
FibroGen: Trial of Pamrevlumab (FG-3019), in Non-Ambulatory Subjects With Duchenne Muscular Dystrophy (DMD). 2015.
Mendell, Jerry R, "Gene therapy for muscular dystrophy: lessons learned and path forward." Neurosci Lett. 2012, 527:90-99.
Pichavant, Christophe. "Current status of pharmaceutical and genetic therapeutic approaches to treat DMD." Mol Ther. 2011, 19:830-840.
Wagner, Kathryn R. "Gentamicin treatment of Duchenne and Becker muscular dystrophy due to nonsense mutations." Ann Neurol. 2001, 49:706-711.
Malik, Vinod. "Gentamicin-induced readthrough of stop codons in Duchenne muscular dystrophy." Ann Neurol. 2010, 67:771-780.
Lee, Meng-Jen. "Andrographolide and 14-deoxy-11,12-didehydroandrographolide from Andrographis paniculata . . . " J Ethnopharmacol. 2010, 132:497-505.
Lee, Tzung-Yan. "Modulation of the cannabinoid receptors by andrographolide attenuates hepatic . . . " Apoptosis. 2010, 15:904-914.
Deluca, Annamaria. "Enhanced dystrophic progression in mdx mice by exercise and beneficial effects . . . " J Pharmacol Exp Ther. 2003, 304:453-463.
Deluca, Annamaria. "A multidisciplinary evaluation of the effectiveness of cyclosporine . . . " Am J Pathol. 2005, 166:477-489.
Cabello-Verrugio, Claudio. "Angiotensin II receptor type 1 blockade decreases CTGF/CCN2-mediated . . . " J Cell Mol Med. 2012, 16:752-764.

* cited by examiner

*Primary Examiner* — Kara R McMillian
(74) *Attorney, Agent, or Firm* — Pharmaceutical Patent Atty's, LLC

(57) ABSTRACT

Andrographolide 70 mg orally twice per day maintains normal health and body function in pediatric patients with Duchenne muscular dystrophy (DMD) and Becker's muscular dystrophy (BMD), and treats DMD/BMD.

18 Claims, 3 Drawing Sheets
(1 of 3 Drawing Sheet(s) Filed in Color)

NATURAL AND SYNTHETIC ANDROGRAPHOLIDES COMPOUNDS FOR THE TREATMENT OF SKELETAL MUSCULAR DYSTROPHIES

RELATED APPLICATIONS

None

GOVERNMENT INTEREST

None

PRIOR DISCLOSURES BY AN INVENTOR

None

INTRODUCTION

The current invention involves the use of andrographolide to maintain normal health and body function in patients with Duchenne muscular dystrophy (DMD) or Becker's muscular dystrophy (BMD), and its use to treat the Duchenne and Becker types of muscular dystrophies.

We here disclose the beneficial effect of said compound in muscle strength, histology and life expectancy, providing a benefit superior to that of prednisone. Our data also shows a significant reduction in the symptoms of disease (pain, the ability to walk/move and to play/run, or jump, and muscle coordination and muscle force) and improvement in quality of life and sleep in children with DMD.

BACKGROUND

Duchenne and Becker muscular dystrophies are an X-chromosome linked, recessive genetic disorder caused by a mutation in the dystrophin gene. The two are differentiated by clinical severity, rather than etiology; DMD is more severe and patients have a shorter life expectancy, while BMD is relatively less severe and patients therefore enjoy a somewhat longer life expectancy. DMD affects about 1 of 3,500 live births. This incidence does not vary significantly based on their country of origin. There is no effective therapy. See Kapsa, R. et al., *Novel Therapies For Duchenne Muscular Dystrophy*, 2 Lancet Neurol 299 (2003). It is caused by the absence of dystrophin, a cytoskeletal protein that anchors the skeletal muscle fiber to the extracellular matrix (ECM). The absence of this protein increases the susceptibility of muscle fiber to rupture caused by the continuous cycles of contraction and relaxation. See Blau, HM. et al., *Defective Myoblasts Identified In Duchenne Muscular Dystrophy*, 80 Proc Natl Acad Sci USA 4856 (1983), Allen, DG. et al., *Duchenne Muscular Dystrophy—What Causes The Increased Membrane Permeability In Skeletal Muscle?*, 43 Int J Biochem Cell Biol 290 (2011).

Of the 650 active muscles, the muscular dystrophy of Duchenne affects all of them. Thus, children with this condition gradually and progressively lose muscle strength, requiring the use of a wheel chair at 10-12 years old. Death can occur in the late second or early third decade of life, often due to cardio-respiratory arrest due to severe muscle damage in the heart and diaphragm muscles. One cause of this damage and loss of muscle function is the appearance of fibrosis, which is characterized by excessive accumulation of ECM replacing muscle tissue by connective tissue, dramatically affecting the fibers environment and therefore normal muscle physiology. This is a devastating disease that has many indirect costs, involving family and inner circle, that needs daily assistance and change of life style. Today there is no cure for DMD and no treatment to fight fibrosis in any tissue.

DMD and BMD have genetic origins. The only currently-known way to restore the gene expression is through Gene and/or Cell therapies. Nevertheless, these therapies represent a major challenge, since muscles are the most abundant tissue in the body and over-fibrosis reduces the efficacy of these approaches. See Zhou, L. et al., *Targeting Fibrosis In Duchenne Muscular Dystrophy*, 69 J Neuropathol Exp Neurol 771 (2010). Therefore, even if current gene therapy trials are successful, they are unlikely to elicit a significant benefit if used in patients at more advanced stages of the disease.

Some DMD pathological features are myofiber atrophy, fatty degeneration, necrosis and fibrosis. Only fibrosis has been correlated through clinical studies with poor motor outcome, as gauged by muscle strength and age at loss of ambulation. See Desguerre, I. et al., *Endomysial Fibrosis In Duchenne Muscular Dystrophy: A Marker Of Poor Outcome Associated With Macrophage Alternative Activation*, 68 J Neuropathol Exp Neurol 762 (2009). This finding supports the notion that fibrosis directly contributes to progressive muscle dysfunction and the lethal phenotype of DMD.

Fibrosis is defined pathologically as an inappropriate repair of connective tissue and is characterized by a loss of normal tissue architecture by dense, homogeneous, and increasingly stable ECM components such as collagens and fibronectin (which can impair tissue function). The process leads to progressive distortion of tissue architecture with consequent dysfunction and ultimate failure of fibrotic organ. See Wynn, TA. et al., *Cellular And Molecular Mechanisms Of Fibrosis*, 214 J Pathol 199 (2008), Varga, J. et al., *Fibrosis Research: Methods And Protocols*, Humana Press (2005). Therefore, finding new drugs and therapies with anti-fibrotic effects is crucial in the field.

Glucocorticoids such as prednisone are the first line therapy in the treatment of DMD, which retards the use of wheelchairs for around 2 to 4 years, but involves severe side effects. The most common assumption is that glucocorticoid treatment of dystrophy alleviates the dystrophic process primarily through immune suppression and reduction of inflammation. However, vertebral fractures are a well-known complication associated with steroid use and should be aggressively treated with bisphosphonate therapy. Verma, S. et al., *Review Of Duchenne Muscular Dystrophy (DMD) For The Pediatricians In The Community*, 49 Clin Pediatr (Phila) 1011 (2010).

Andrographolide (CAS 5508-58-7) is a bicyclic diterpenoid lactone. Its IUPAC systemic name is 3-[2-[Decahydro-6-hydroxy-5-(hydroxymethyl)-5,8a-dimethyl-2-methylene-1-napthalenyl]ethylidene]dihydro-4-hydroxy-2(3H)-furanone.

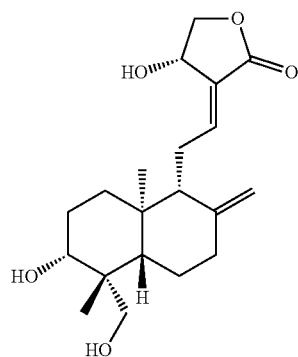 [SMILES: C=C1CC[C@@H]2[C@](C)(CO)[C@H](O)CC[C@@]2(C)[C@@H]1C/C=C1/C(=O)OC[C@H]1O]

Andrographolide has several known analogs and derivatives such as 14-deoxy andrographolide, 9-dehydro-17-hydro andrographolide and sodium 9-dehydro-17-hydro andrographolide-19-yl sulfate. For simplicity, in the appended legal claims we use the term "andrographolide" to encompass 3-[2-[Decahydro-6-hydroxy-5-(hydroxymethyl)-5,8a-dimethyl-2-methylene-1-napthalenyl]ethylidene]dihydro-4-hydroxy-2(3H)-furanone) and structurally-similar compounds that provide a functionally-similar benefit.

Andrographolide significantly reduces muscle associated fibrosis, in an animal model of DMD, the mdx mouse. Former studies have evaluated the effect of andrographolide in vivo in a model of DMD the mdx mouse and the results show that the compound is able to inhibit the expression of pro-fibrotic factor CTGF in vitro (skeletal cells), increase exercise resistance in dystrophic mice and skeletal muscle force in dystrophic muscles. See Cabrera, D. et al., *Andrographolide Attenuates Skeletal Muscle Dystrophy In MDX Mice And Increases Efficiency Of Cell Therapy By Reducing Fibrosis*, 4 *Skelet Muscle* (2014).

We now have human clinical data showing that andrographolide and certain of its analogs can preserve muscular strength in animal models of skeletal muscular dystrophies, and preserve quality of life in human children suffering Duchenne muscular dystrophy. This type of strategy is completely new, since no compound has shown efficacy in the treatment of human skeletal muscular diseases.

SKELETAL MUSCULAR DYSTROPIES

Skeletal muscular diseases correspond to a wide group of disorders affecting skeletal muscle strength, capability to move, breadth and some of them affect cardiac function. These diseases can be grouped in three categories.

SKELETAL MUSCULAR DYSTROPHIES include DMD; Becker muscular dystrophy; Congenital muscular dystrophies (CMD); Bethlem CMD; Fukuyama CMD; Muscle-eye-brain diseases; Rigid spine syndromes; Ullrich CMD; Walker-Warburg syndromes; Emery-Dreifuss muscular dystrophy; Facioscapulohumeral muscular dystrophy; Limb-girdle muscular dystrophies; Myotonic dystrophy; Oculopharyngeal muscular dystrophy.

MOTOR-NEURON DISEASES include Amyotrophic lateral sclerosis; Spinal-bulbar muscular atrophy; and Spinal muscular atrophy.

INFLAMMATORY MYOPHATIES include Dermatomyositis; Inclusion-body myositis; and Polymyositis.

DMD/BMD is the most common genetic muscle disease. Although gene therapy and cell therapy may ultimately provide a cure for DMD/BMD, currently the disease is devastating, with no existing effective therapies. Recent studies have demonstrated that ameliorating muscle fibrosis may represent a viable therapeutic approach for DMD. See Zhou, L. et al., *Targeting Fibrosis In Duchenne Muscular Dystrophy*, 69 *J Neuropathol Exp Neurol* 771 (2010), Serrano, AL. et al., *Fibrosis Development In Early-Onset Muscular Dystrophies: Mechanisms And Translational Implications*, 64 *Semin Cell Dev Biol* 181 (2017).

Therapies for Duchenne and Becker Muscular Dystrophies

Mendell et al. discusses different emerged therapeutic strategies that have been used in pre-clinical and clinical settings. Most attractive are molecular-based therapies that can express the missing dystrophin protein. See Mendell, JR. et al., *Molecular Therapies Strategies Targeting Duchenne Muscular Dystrophy*, 25 *J Child Neurol* 1145 (2010).

However, it has been difficult to bring these therapies to clinical assays, because dystrophin is a big protein and moreover a large gene, therefore to find good vectors to deliver the gene is troublesome. The efficacy of these approaches is very low. The size of the dystrophin gene makes it difficult to work with gene therapy. Thus smaller genes, micro or mini-dystrophin, have been developed, which can be inserted into a vector. The most suitable vector found so far is a virus associated with the adenovirus, a non-pathogenic parvovirus, but has shown to cause an immunological response. In order to assess the response, mdx mice dys-/dys- have been created, and there is evidence that when the gene is injected, the dystrophin is partially expressed and muscular strength is improved. However, in preliminary studies on humans, 90 days after treatment the gene expression was lost. See Mendell, JR. et al., *Molecular Therapies Strategies Targeting Duchenne Muscular Dystrophy*, 25 *J Child Neurol* 1145 (2010), Arechavala-Gomeza, V. et al., *Revertant Fibres And Dystrophin Traces In Duchenne Muscular Dystrophy: Implication For Clinical Trials*, 20 *Neuromuscul Disord* 295 (2010). These results suggest that cellular immunity inhibits the success of this therapy.

Other approaches include increasing the strength of muscles (myostatin inhibitors), reducing muscle fibrosis and decreasing oxidative stress. Additional targets include inhibiting NF-κB to reduce inflammation or promoting skeletal muscle blood flow and muscle contractility using phosphodiesterase inhibitors or nitric oxide (NO) donors. Nonetheless, these approaches only control the symptoms, but not the primary cause of DMD dystrophies that is the absence of dystrophin gene expression, therefore the disease is less severe but not healed. In the same line, it has been shown that one of the pro-fibrotic factors corresponds to Connective Tissue Growth Factor (CTGF/CCN29. Over-expression of CTGF in wild type muscle, induces a dystrophic phenotype, despite the presence of dystrophin. See Morales, MG. et al., *CTGF-CCN-2 Over-Expression Can Directly Induce Features Of Skeletal Muscle Dystrophy*, 225 *J Pathol* 490 (2011). Furthermore, inhibition of CTGF in the mdx mouse model, using antibodies against CTGF result in an improvement of skeletal muscle strength, reduction of skeletal muscle degeneration and better histology of the dystrophic skeletal muscle. See Morales, MG. et al., *Reducing CTGF-CCN2 Slows Down MDX Muscle Dystrophy And Improves Cell Therapy*, 22 *Hum Mol Genet* 4938 (2013). Currently a phase II using CTGF antibodies in patients with DMD is ongoing. See Fibrogen et al., *Trial Of Pamrevlumab (FG-3019), In Non-Ambulatory Subjects With Duchenne Muscular Dystrophy (DMD)*, (2015).

Mendell et. al. used small molecules for exon skipping and mutation suppression and gene transfer to replace or provide surrogate genes as tools for molecular-based approaches for the treatment of muscular dystrophies. Exon skipping is targeted at the pre-mRNA level allowing one or more exons to be omitted to restore the reading frame. In DMD, clinical trials have been performed with two different oligomers, a 2'O-methyl-ribo-oligonucleoside-phosphorothioate and a phosphoro-diamidatemorpholino. Both have demonstrated early evidence of efficacy. See Mendell, JR. et al., *Gene Therapy For Muscular Dystrophy: Lessons Learned And Path Forward*, 527 *Neurosci Lett* 90 (2012). A disadvantage of this drug is that the effect is only transitory and limited to the time in which this antisense oligonucleotide remains in the tissue.

Another molecular approach involves suppression of stop codons to promote reading through of the DMD gene. See Pichavant, C. et al., *Current Status Of Pharmaceutical And*

*Genetic Therapeutic Approaches To Treat DMD*, 19 *Mol Ther* 830 (2011). In cell cultures, gentamicin interacts with the 40S ribosomal subunit in the transcription of RNA, suppressing the termination codons and inserts in its place another amino acid. In studies on mdx mice and in humans, gentamicin was capable of producing dystrophin expression in muscle fibers 20% above normal levels. See Pichavant, C. et al., *Current Status Of Pharmaceutical And Genetic Therapeutic Approaches To Treat DMD*, 19 *Mol Ther* 830 (2011). In studies on mdx mice and humans, gentamicin was capable of producing dystrophin expression in muscle fibers 20% above normal levels. See Pichavant, C. et al., *Current Status Of Pharmaceutical And Genetic Therapeutic Approaches To Treat DMD*, 19 *Mol Ther* 830 (2011).

However, studies on DMD patients remain controversial. In fact, one of them showed a beneficial effect on muscle strength and a re-expression of dystrophin in muscles, while another study in 12 DMD patients over a six-month period, dystrophin expression was detected in only 6 of the 12 patients, and no clinical benefits were observed. See Wagner, KR. et al., *Gentamicin Treatment Of Duchenne And Becker Muscular Dystrophy Due To Nonsense Mutations*, 49 *Ann Neurol* 706 (2001), Malik, V. et al., *Gentamicin-Induced Readthrough Of Stop Codons In Duchenne Muscular Dystrophy*, 67 *Ann Neurol* 771 (2010).

Andrographolide and Fibrotic Disorders

Lee MJ et. al. studied the anti-diabetic nephropathy effect of diterpene lactones-andrographolide (AP1) and 14-deoxy-11, 12-didehydro-andrographolide (AP2). See Lee, MJ. et al., *Andrographolide And 14-deoxy-22, 12-didehydroandrographolide From Andrographis Paniculata Attenuate High Glucose-Induced Fibrosis And Apoptosis In Murine Renal Mesangeal Cell Lines*, 132 *J Ethnopharmacol* 497 (2010). The authors suggested that AP1 or AP2 reduced the phenotypes indicating diabetic nephropathy in MES-13 cells. The compound AP2 showed a more potent activity than AP1 in the reduction of apoptosis marker caspase-3, fibrosis marker TGF-β1, and PAI-1. Furthermore, AP1 and AP2 do not have antioxidant ability in a cellular environment; however, addition of AP1 and AP2 reduced intracellular oxidative states in high glucose cultured MES-13 cells. Lee TY, et. al. have identified andrographolide as a potent protector against cholestasis-induced apoptosis in vivo. Its anti-apoptotic action largely relies on the inhibition of the oxidative stress pathway. See Lee, TY. et al., *Modulation Of The Cannabinoid Receptors By Andrographolide Attenuates Hepatic Apoptosis Following Bile Duct Ligation In Rats With Fibrosis*, 15 *Apoptosis* 904 (2010). These therapies, however, do not have the ability to restore healthy gene expression. A plethora of different strategies have been used to restore the dystrophin expression, nonetheless no one of them has proved fully effective yet.

In contrast, our data surprisingly show that andrographolide can preserve and even improve muscular strength, life expectancy and quality of life of children suffering DMD.

BRIEF DESCRIPTION OF THE FIGURES

The patent or application file contains at least one drawing executed in color. Copies of this patent or patent application publication with drawing(s) will be provided by the Office upon request and payment of the necessary fees.

FIG. 1A presents data for a single electro-stimulation to produce maximal switch force, expressed in $N/cm^2$. FIG. 1B presents data for high frequency stimulation to produce tetanic contraction, expressed as a percentage of peak tetanic force.

DETAILED DESCRIPTON

Example 1

METHODS

Animals and Experimental Exercise

Figure 1:
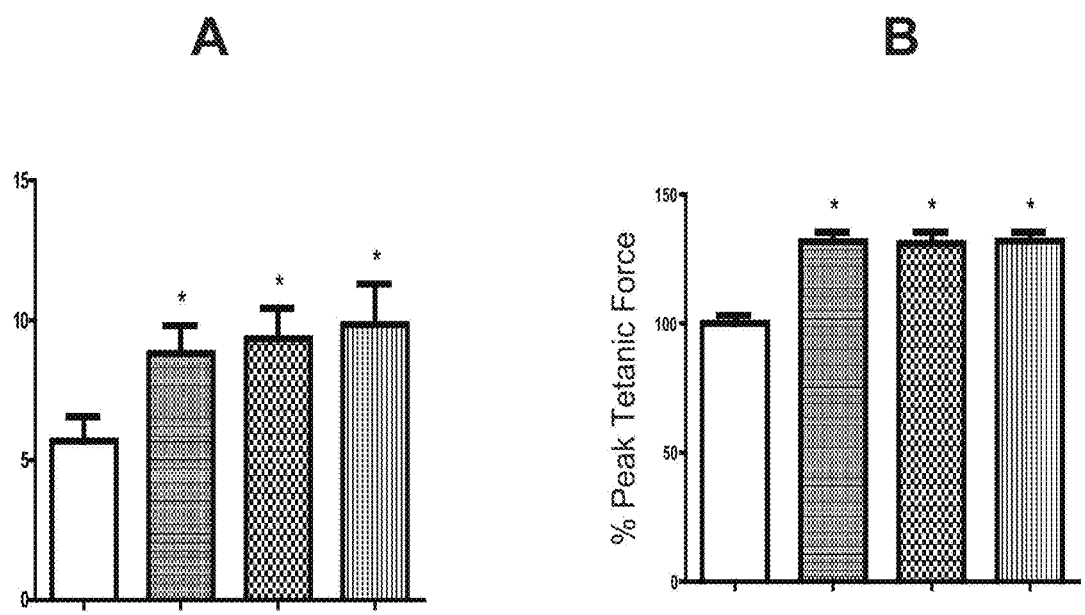
FIG. 1 compares mdx mouse isolated muscle strength generated after treatment with vehicle (column 1), andrographolide (column 2), prednisone (column 3) and andrographolide and prednisone (column 4).

We used 12-week-old control or mdx male mice of the C57BL/10 ScSn strain. The animals were kept at room temperature with a 24-hour night-day cycle and were fed with pellets and water ad libitum. Experimental exercise involved running the mice on a treadmill three times per week for 30 minutes each session at 12 m/minute over three or four months. See Morales, MG. et al., *Reducing CTGF/CCN2 Slows Down MDX Muscle Dystrophy And Improves Cell Therapy*, 22 *Hum Mol Genet* 4938 (2013), DeLuca, A. et al., *Enhanced Dystrophic Progression In MDX Mice By Exercise And Beneficial Effects Of Taurine And Insulin-Like Growth Factor*-1, 304 *J Pharmacol Exp Ther* 453 (2003), DeLuca, A. et al., *A Multidisciplinary Evaluation Of The Effectiveness Of Cyclosporine A In Dystrophic MDX Mice*, 166 *Am J Pathol* 477 (2005), Cabello-Verrugio, C. et al., *Angiotensin II Receptor Type* 1 Blockade CTGF/CCN2-*Mediated Damage And Fibrosis In Normal And Dytrophic Skeletal Muscles*, 16 *J Cell Mol Med* 752 (2012). Four experimental groups were designed: animals in the first group were injected intraperitoneally (ip) with andrographolide (1.0 mg/kg/day). Animals in the second group were treated with prednisone (5 mg/kg). Third group, animals were treated with prednisone together with andrographolide. Fourth group animals were injected with saline. At the end of the experiment the muscles were dissected and removed under anesthesia (isofluorane gas) and then the animals were sacrificed. Tissues were used for electrophysiological measurement or rapidly frozen and stored at −80° C. until processing. All protocols were conducted in strict accordance with guidelines and with the formal approval of the Animal Ethics Committee of the Pontificia Universidad Católica de Chile.

Skeletal Muscle Histology and Indirect Immunofluorescence.

Architecture and histology were detected by hematoxylin-eosin (H&E) stain in transverse sections of muscle. See Morales, MG. et al., *CTGF/CCN-2 Over-Expression Can Directly Induce Features Of Skeletal Muscle Dystrophy*, 225

*J Pathol* 490 (2011). Collagen Type I was determined as described in Morales, MG. et al., *Reducing CTGF/CCN2 Slows Down MDX Muscle Dystrophy And Improves Cell Therapy*, 22 Hum Mol Genet 4938 (2013).

Contractile Properties

The isometric force of isolated muscles was measured as described previously [30]. Briefly, optimum muscle length (Lo) and stimulation voltage were determined from micromanipulation of muscle length to produce maximum isometric twitch force. Maximum isometric tetanic force (Po) was determined from the plateau of the frequency-force relationship after successive stimulations at 1 to 200 Hz for 450 ms, with 2-minute rests between stimuli. After determination of isometric contractile properties, muscles were subjected to a 3 repeated tetanic stimulation protocol. Muscles at Lo were maximally stimulated for 450 ms once every 5 seconds. After functional testing, muscles were removed from the bath, trimmed of their tendons and any adhering non-muscle tissue, blotted once on filter paper, and weighed. Muscle mass and Lo were used to calculate specific net force (force normalized per total muscle fiber cross-sectional area (CSA), mN/mm2). See Morales, MG. et al., *CTGF/CCN-2 Over-Expression Can Directly Induce Features Of Skeletal Muscle Dystrophy*, 225 *J Pathol* 490 (2011).

Life Expectancy

Groups of mdx mice were treated with or without andrographolide (1.0 mg/kg/day) 3 times per weeks starting at one month old until they die naturally. The animals were maintained under free food and water access all the time. Days of death was recorded.

Patients Suffering Duchenne Muscular Dystrophy

Thirteen pediatric patients were derived from the Chilean Duchenne Association with confirmed clinical diagnostic. Of the thirteen patients, seven of them used chronic glucocorticoid treatment (Table A). Two of the patients had disease advanced enough so that the patients were no longer ambulatory.

TABLE A

Age distribution and corticosteroids usage in Duchenne muscular dystrophy patients

| Age (years | Corticosteroids | WC |
| --- | --- | --- |
| 4 | − | |
| 4 | − | |
| 5 | − | |
| 6 | + | |
| 6 | + | |
| 7 | + | |
| 7 | − | |
| 8 | + | |
| 8 | + | |
| 9 | − | |
| 9 | + | WC |
| 13 | + | |
| 14 | − | WC |

WC = wheel chair

All patients, both those treated with glucocorticoid and those not requiring glucocorticoid, received 70 mg andrographolide (as a standardized extract) orally two times per day. Treatment periods ranged from one month to more than twelve months. Each patient had a parent or mentor who completed a questionnaire indicating their observations, ranked accordingly a scale from 0 to 5, for different aspects such as: quality of life; quality of sleep; intensity of pain (if any); intensity of cold/chilly sensation, the ability to walk or move, the ability to jump, gross-muscle coordination, force (strength) and mood. (Table B)

TABLE B

PedsQL for Duchenne Muscular Dystrophy Module

| Score | Observation |
| --- | --- |
| 0 | Worse than Before |
| 1 | No Change |
| 2 | Slight Improvement |
| 3 | Important Improvement |
| 4 | Extraordinarily Better |

EXAMPLES

ANIMAL STUDIES

EXAMPLE 1. Effect of Andrographolide and Prednisone on Skeletal Muscle Strength in Dystrophic Mice.

FIG. 1 shows the isolated muscle strength generated from mdx mice treated or not with andrographolide, prednisone or the combination of both compounds under two types of stimuli: A) Single electro-stimulation to produce maximal switch force and B) High frequency stimulation to produce tetanic contraction. Under both experimental conditions, muscles from mdx mice treated with andrographolide show improved muscle contraction at similar levels than the induced by prednisone. Interestingly, we did not find a synergistic effect when both treatments were used concomitantly. These results shows that, in terms of improving muscle strength, andrographolide is as efficient as prednisone. This suggests that andrographolide might replace prednisone treatment.

EXAMPLE 2. Effect of Andrographolide and Prednisone on Dystrophic Skeletal Muscle Damage.

Figure 2:
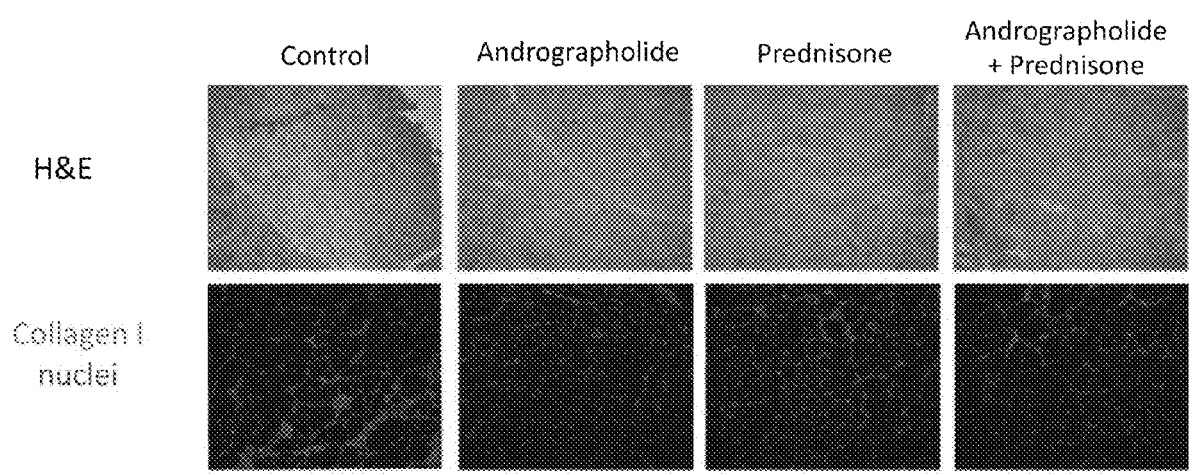
FIG. 2 presents photographs of mouse muscle histology in 12 week old mdx exercised mice treated for 3 months with prednisone and/or andrographolide. Top row shows that both andrographolide and prednisone prevent the increase of damaged areas observed in the muscles of dystrophic mdx mice compared to vehicle-treated mdx mice. Both compounds together produce the same improvement as each compound separately, indicating a competitive effect on the same receptor or on the same pathway. Top row corresponds to H&E staining. Bottom row shows that andrographolide and prednisone treatment each diminish fibrosis to the same extent. Bottom row, uses indirect immunofluorescence for collagen type I.
Figure 3:
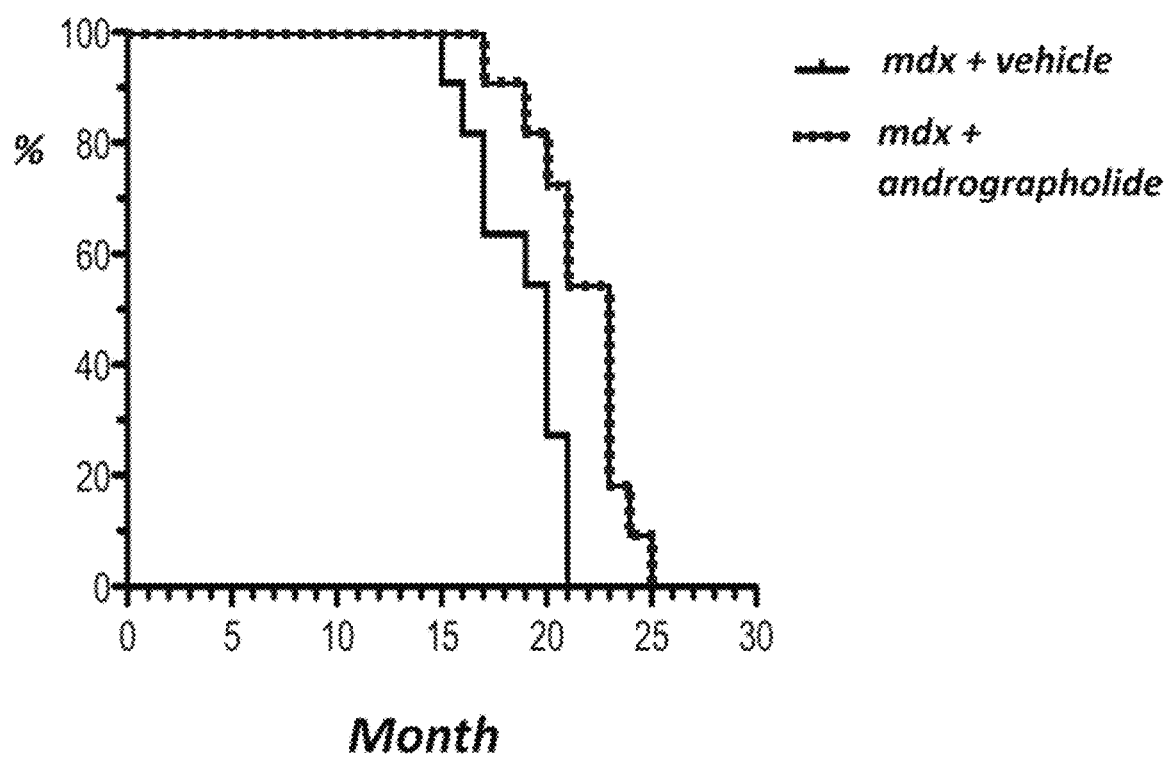
FIG. 3 presents a Kaplan-Meier curve for mdx mice showing percent alive over time, for mice treated with placebo (n=6) and with andrographolide (n=6). Andrographolide treatment increased survival time.

To evaluate if andrographolide or prednisone had an effect on the dystrophic phenotype of mdx mice we evaluate through Hematoxylin and Eosin staining, the histology of the tibialis anterior muscle from WT, vehicle-treated mdx, andrographolide-treated mdx mice, prednisone-treated mdx mice and andrographolide together with prednisone after 3 months administration. FIG. 2 (top row) shows that both andrographolide and prednisone administration prevented the increase of damaged areas observed in the muscles of dystrophic mdx mice compared to vehicle-treated mdx mice. Both compounds together have the same improvement compared to each added separately. FIG. 2 (bottom row) shows that andrographolide and prednisone each diminish fibrosis, and do so to the same extent. Tissue samples evaluated using collagen type I immuno-staining. These results indicate that andrographolide and prednisone improves the architecture of dystrophic skeletal muscles and decrease fibrosis. We posit that this prevents tissue damage in mdx mice.

EXAMPLE 3. Effect of Andrographolide on Survival Percentage in MDX Mice.

To evaluate whether andrographolide affects survival in dystrophic mice we perform a long term treatment with andrographolide through intra-peritoneal injections, three times per weeks starting at one month old until they die naturally, in order to determine the effects over life expectancy in mdx mice. The results showed that mdx mice treated over their entire life with andrographolide have a total life expectancy around 21.7±2.35 months, while mdx mice treated with vehicle was 18.8±2.09 months.

Andrographolide Increases Life Expectancy of Dystrophic Mice by 15%.

HUMAN STUDIES

Thirteen (13) children with DMD of different ages (ranging from 4 to 14 years old) were treated with Andrographis paniculata capsules (either taking corticosteroids or not) for a variable period of time (ranging from one month to two years) (Table A).

Each parent or tutor received a questionnaire with different scores parameters to be completed. The parents were asked to fill out the Pediatric Quality of Life Inventory TM questionnaire (*PedsQL for Duchenne Muscular Dystrophy Module*) of their perception about; Quality of life, Sleep, Pain, Cold, Walk/Move, Play/Run, Jump, Coordination, Force and Mood of children during Andrographis paniculata treatment (Table B).

The PedsQL average scores for the above parameters is shown in Table C. In all the cases, Andrographis paniculata capsules had a positive effect over time. The highest improvement was seen in quality of life, quality of sleep, decrease of pain, decrease of frequency of colds, coordination, force and mood. Slight improvement was seen in the ability in play, walk and jump. The patients who began the study requiring a wheelchair continued to require a wheel chair throughout the study period.

TABLE C

PedsQL average scores in patients with Duchenne Muscular Dystrophy

| Parameter | Treatment Duration (months) | | | | | | |
|---|---|---|---|---|---|---|---|
| | 0 | 1 | 3 | 6 | 9 | 12 | >12 |
| Quality of Life | 0 | 1.7 | 3.1 | 2.7 | 3.0 | 2.0 | 2.5 |
| Quality of sleep | 0 | 2.0 | 2.1 | 3.0 | 2.3 | 2.7 | 3.0 |
| Pain | 0 | 1.5 | 2.2 | 3.3 | 3.3 | 2.3 | 3.0 |
| Cold sensation | 0 | 1.8 | 2.2 | 3.0 | 2.7 | 3.3 | 2.5 |
| Walk/Move | 0 | 1.8 | 2.6 | 2.0 | 2.7 | 2.3 | 2.5 |
| Play/Run | 0 | 1.8 | 2.5 | 2.0 | 2.5 | 2.3 | 2.5 |
| Jump | 0 | 1.8 | 2.3 | 2.0 | 2.0 | 2.0 | 2.5 |
| Coordination | 0 | 1.6 | 2.5 | 2.3 | 3.0 | 2.0 | 2.5 |
| Force | 0 | 1.7 | 2.1 | 2.7 | 3.3 | 2.0 | 1.5 |
| Mood | 0 | 2.0 | 2.1 | 3.0 | 3.0 | 1.7 | 2.5 |

We can conclude that Duchenne muscular dystrophy patients receiving andrographolide 70 mg orally twice per day show important improvement in several aspects such as quality of life and sleep, decrease in pain and cold episodes, increase in coordination, force as well as improvement of mood. The progress ranged from slight to important improvement and was observed in all 13 patients (independently of the age) that received treatment. The progress in the above parameters was clearly observed after the third month of treatment, independently of the age of the patient. These results strongly indicate that treatment provides a novel and effective approach to maintain or improve quality of life, strength and coordination in patients suffering Duchenne Muscular Dystrophy and Becker's muscular dystrophy.

We claim:

1. A method comprising: diagnosing Duchenne or Becker's muscular dystrophy in a human, and then providing to the human an oral formulation of andrographolide, said oral formulation including an amount of ardrographolide effective to maintain healthy function in the human or treat at least one symptom of Duchenne or Becker's muscular dystrophy.

2. The method of claim 1, wherein the oral formulation includes an amount of andrographolide effective to treat at least one symptom of Duchenne or Becker's muscular dystrophy.

3. The method of claim 2, wherein the oral formulation includes an amount of andrographolide effective to improve quality of life.

4. The method of claim 2, wherein the oral formulation includes an amount of andrographolide effective to improve quality of sleep.

5. The method of claim 2, wherein the oral formulation includes an amount of andrographolide effective to reduce DMD/BMD associated pain.

6. The method of claim 2, wherein the oral formulation includes an amount of andrographolide effective to reduce DMD/BMD associated perception of cold.

7. The method of claim 2, wherein the oral formulation includes an amount of andrographolide effective to improve the ability to walk or move.

8. The method of claim 2, wherein the oral formulation includes an amount of andrographolide effective to improve the ability to play or run.

9. The method of claim 2, wherein the oral formulation includes an amount of andrographolide effective to improve the ability to jump.

10. The method of claim 2, wherein the oral formulation includes an amount of andrographolide effective to improve muscular coordination.

11. The method of claim 2, wherein the oral formulation includes an amount of andrographolide effective to improve muscular force.

12. The method of claim 2, wherein the oral formulation includes an amount of andrographolide effective to improve mood.

13. The method of claim 1, wherein the oral formulation includes an amount of andrographolide effective to maintain healthy function in the human.

14. The method of claim 1, where said human is not more than 21 years of age.

15. The method of claim 1, where said amount of andrographolide is about 140 mg a day.

16. The method of claim 15, wherein said andrographolide is administered as two 70 mg doses per day.

17. The method of claim 1, where said amount andrographolide is about 0.8 to about 5.5 mg/kg of patient body weight a day.

18. The method of claim 17, where said andrographolide is administered as two doses per day, each dose comprising about 0.4 to about 2.75 mg/kg of patient body weight per day.

\* \* \* \* \*